| United States Patent [19] | [11] Patent Number: 4,799,882 |
| Kesling | [45] Date of Patent: Jan. 24, 1989 |

[54] EDGEWISE BRACKET

[75] Inventor: Peter C. Kesling, LaPorte, Ind.

[73] Assignee: TP Orthodontics, Inc., Westville, Ind.

[21] Appl. No.: 122,066

[22] Filed: Nov. 17, 1987

[51] Int. Cl.$^4$ ............................................. A61C 7/00
[52] U.S. Cl. ...................................................... 433/8
[58] Field of Search .................... 433/8, 9, 10, 11, 12, 433/13, 14

[56] References Cited

U.S. PATENT DOCUMENTS

3,626,593 12/1971 Ridgeway .............................. 433/11
3,854,207 12/1974 Wildman ................................ 433/11
4,415,330 11/1983 Daisley et al. .
4,659,309 4/1987 Merkel .

Primary Examiner—Robert Peshock
Attorney, Agent, or Firm—Lloyd L. Zickert

[57] ABSTRACT

An orthodontic bracket of the edgewise type including a single tie wing having a labially facing archwire slot and a scoopout or pocket along the archwire slot axis formed so that the archwire slot is interrupted centrally of the tie wing so as to reduce the friction between the archwire and the bracket along the longitudinal axis of the archwire. The tie wing may optionally include one or more notches at the edges of the tie wing tips wherein the notches are sized to receive an elastomeric ligature.

24 Claims, 3 Drawing Sheets

EDGEWISE BRACKET

DESCRIPTION

This invention relates in general to an improved orthodontic bracket of the edgewise type which is more comfortable and which reduces archwire friction by reducing the length of the archwire slot, and more particularly to a single tie wing bracket structured to facilitate the use of elastomeric ligatures to achieve desired tooth movement.

BACKGROUND OF THE INVENTION

Heretofore, it has been well known to provide edgewise brackets having a single tie wing with a labially facing archwire slot, and it has been believed that the continuous slot extending between the mesial and distal sides of the bracket has interfered with efficient tooth movement objectives because of the friction generated between the archwire and the bracket which may inhibit smooth sliding movement of the bracket along the archwire.

While it is also well known that a single tie wing bracket is usually stronger than a double tie wing bracket, bracket strength is often sacrificed for the double wing bracket in order to permit a ligature to be applied to one of the wings during treatment to achieve desired tooth movement in relation to other teeth. Sacrificing bracket strength can lead to bracket failure which interrupts and extends the treatment time.

It is also known that with the standard double wing edgewise bracket, some discomfort may be experienced because of the relatively narrow gingival and incisal edges of the tie wing tips and the relatively large distances between the tie wing tips defined by this configuration. Typical edgewise brackets of this type are illustrated in U.S. Pat. Nos. 4,415,330 and 4,659,309.

SUMMARY OF THE INVENTION

The recent advent of making brackets by metal casting methods has produced a bracket making technology that has provided new possibilities for bracket structure. Heretofore, it has been known to mold plastic brackets and that their use is limited because the strength of a plastic bracket is not nearly as high as a metal bracket and more failures are known. An investment cast metal bracket has nearly the same strength as the heretofore well known metal brackets that are made by machining techniques from a solid piece. At least it is recognized that a metal cast bracket has substantially greater strength than a plastic bracket and sufficient strength to resist breakdown during normally encountered usage. It is also known that an investment cast bracket can be more readily shaped as desired.

The bracket of the present invention may be made by a combination of metal casting and machining in that the body of the bracket may be cast and the archwire slot thereafter machined or cut in the body at the labial face to provide the precise dimension of the slot. It is also possible to completely metal cast the bracket by additionally casting the slot, which requires one mold for each type of slot. The bracket of the invention overcomes the difficulties heretofore encountered in edgewise brackets with respect to the above mentioned elements of archwire friction, overall strength, and patient comfort.

The bracket includes a scoopout or pocket formed centrally between the opposite ends of the archwire slot to define a segmental archwire slot in a single tie wing bracket, thereby reducing the slot surfaces that receive the wire and therefore the contact and sliding friction between the bracket and the archwire. This feature tends to enhance the efficiency of the bracket during the treatment of a patient to thereby reduce the time needed for effecting a desired tooth movement. Reducing friction between the archwire and the bracket also tends to produce faster treatment and reduce overall treatment time, thereby enhancing overall patient comfort. Improvement of patient comfort usually greatly improves patient cooperation, which, in turn, usually produces better end results.

Because the bracket of the invention is a single tie wing bracket, it retains the general strength factor of heretofore known single wing brackets even though the tie wing may be notched for receiving elastomeric ligatures. Thus, where notching permits the use of ligatures along the bracket to achieve the location desired for particular tooth movement and similar objectives previously attained by plural tie wing brackets, the bracket also retains the general strength characteristics of a single tie wing bracket.

Since the bracket of the invention is a generally single tie wing bracket and is metal cast to provide smoother edges facing occlusally and gingivally and a smoother labial face, it is more comfortable to the patient. Such an increase in the comfort level additionally enhances patient cooperation.

It is therefore an object of the present invention to provide a new and improved edgewise bracket that reduces archwire friction, while providing substantially the same strength as a single wing bracket with plural wing advantages and increasing the comfort level of the patient to thereby enhance patient cooperation.

Another object of the present invention is in the provision of a metal cast bracket with a scoopout or pocket opening labially of the tie wing and along the archwire slot to reduce friction between the archwire and the bracket by reducing the area of contact between the archwire and the archwire slot.

Still another object of the present invention is in the provision of a metal cast bracket which has a single wing configuration with notches in the wing tips to obtain the generally known strength level of a single wing bracket while having the capability of receiving ligatures in a fashion similar to double wing brackets.

A still further object of the present invention is in the provision of an orthodontic bracket of the edgewise type having a single tie wing with notches in the tie wing tips to provide the advantages of plural wing brackets and which includes rounded and smooth edges facing occlusally, gingivally, mesially and distally, and relatively smooth labial free, thereby enhancing patient comfort which promotes patient cooperation.

Other objects, features and advantages of the invention will be apparent from the following detailed disclosure, taken in conjunction with the accompanying sheets of drawings, wherein like reference numerals refer to the parts.

DESCRIPTION OF THE INVENTION

The bracket of the present invention is of the edgewise type and may be made from a combination investment casting procedure and slot-cutting procedure or from a pure casting procedure where the slot would be cast. While the bracket is preferably made of metal, it should be appreciated that it could be molded of plastic. It also could be molded or otherwise made of a suitable ceramic material.

The bracket is of a single tie wing configuration to maximize strength and may be formed with notches in the tie wing tips for accommodating ligatures of the wire or elastomeric type to provide some of the desired functions for tooth movement as are present with brackets having plural tie wings.

The strength of the bracket of the invention is such that it minimizes failure, thereby enhancing the efficiency of the bracket. By minimizing failure, treatment time is reduced and patient cooperation is also enhanced.

The overall shape of the bracket is such as to provide better comfort for the patient by rounding edges and providing relatively continuous exteriors. Again, increased comfort enhances patient cooperation. These brackets are very small; and knowing the bracket to be streamlined, the patient at least psychologically believes such to enhance his or her appearance.

Referring now to the drawings, and particularly to the embodiment of FIGS. 1 to 4, the bracket of the invention, generally designated by the numeral 15, is shown mounted on a base or pad 16. While the base 16 is of a type that will be suitable for directly bonding the bracket to a tooth, it may take any desired form having a bonding surface that will enhance the bonding to a tooth with a suitable adhesive. The base may be integrally formed with the bracket but preferably separately formed and suitably secured to the bracket by soldering, welding or other means. Further, it may be appreciated that the base may be suitably contoured for a particular tooth. By making the bracket as a separate element, it will also be understood that it could be attached to a band if desired, which would in turn be suitably cemented to a tooth.

Figure 1:
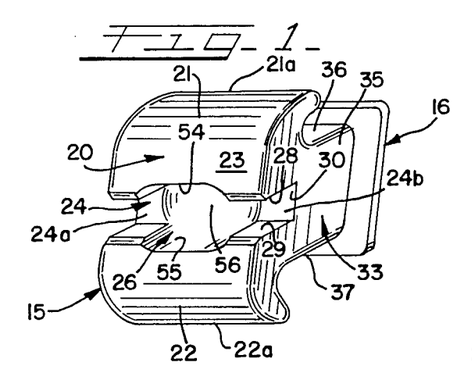
FIG. 1 is a perspective view of one form of the bracket of the present invention with a single tie wing and no notches in the tie wing tips.
Figure 2:
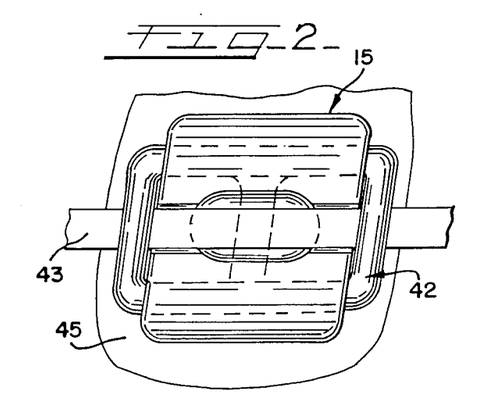
FIG. 2 is a front elevational view of the bracket of FIG. 1 mounted on a tooth and having an archwire received in the slot and retained therein with an elastomeric ligature retaining the archwire in place.
Figure 3:
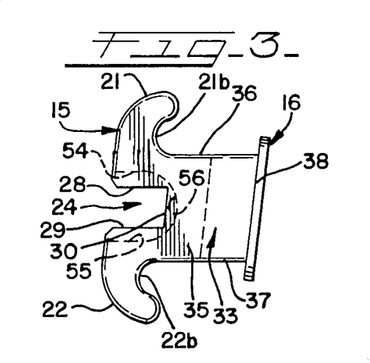
FIG. 3 is a side elevational view of the bracket shown in FIG. 1.

The bracket 15 includes a single tie wing 20 having upper and lower tie wing tips 21 and 22. At the labial or buccal face 23 of the tie wing, a horizontally extending and labially opening archwire slot 24 is formed centrally of the tie wing to define the substantially equally sized tie wing tips 21 and 22. Centrally of the tie wing and along the archwire slot 24, a scoopout or pocket 26 is formed, thereby defining spaced archwire slot segments 24a and 24b. Depending upon the location of the bracket in the mouth, one of the segments will be mesial and the other distal. The segments 24a and 24b will be in precise alignment whereby in this embodiment the upper and lower horizontal walls of the segments will be coplanar and parallel to each other and the bottom walls of the segments will be coplanar and extend normally parallel to the wall of the bracket normally secured to the base 16. In some brackets the bottom wall will be perpendicular to the opposed walls of the slot, and in some brackets, depending upon the torque of the bracket, the bottom wall will extend at an angle to the opposed walls. More particularly, as seen in FIG. 3, the archwire slot 24 includes opposed parallel walls 28 and 29 and a bottom wall 30. Depending upon the mounting of a bracket on a tooth, one of the opposed walls will be the gingival wall and the other the occlusal wall. As illustrated in FIGS. 1 to 4, the upper wall 28 will be the gingival wall and the lower wall 29 will be the occlusal wall. The bracket 15, while illustrated as being mounted on an upper left canine, could be used on any tooth.

Lingual to the labiobuccal face 23 of the tie wing is the base portion 33 defined by opposed parallel walls 34 and 35 and opposed parallel walls 36 and 37. Walls 34 and 35 will constitute the mesial and distal walls depending upon the location of the bracket in the mouth of a patient, while the opposed walls 36 and 37 will constitute the gingival and occlusal walls depending upon where it is to be mounted.

It will be noted that the upper and lower walls 28 and 29 are parallel to th upper and lower base portion walls 36 and 37 and that the bottom wall 30 of the archwire slot is parallel to the back wall 38 of the base portion. It will also be noted that the upper edge 21a of the upper tie wing tip 21 and the lower edge 22a of the lower tie wing tip 22 are parallel to each other and also parallel to the upper and lower walls of the archwire slot and the upper and lower walls of the base portion 33. However, it is not necessary that the edges be parallel to each other.

The tie wing tips 21 and 22 project rearwardly or lingually to define hooks for ligatures as noted at 21b and 22b in FIG. 3. Thus, ligature ties of the metal or elastomeric type may be received by the hook portions of the tie wing tips to secure an archwire in place in the archwire of the bracket. Preferably, elastomeric ligatures of the well known type as ligature 42 in FIG. 2 are used to retain an archwire 43 in place on a bracket, such a illustrated in FIG. 2. The bracket 15 is also illustrated as being mounted on a canine tooth 45 in FIG. 2. When mounting an archwire on a bracket, it is first placed in the archwire slot and then an elastomeric ligature is hooked over one ear or tie wing tip of the bracket, pulled over the bracket face and across the archwire at the mesial and distal sides of the bracket and then hooked over the other tie wing, as illustrated in FIG. 2.

Figure 4:
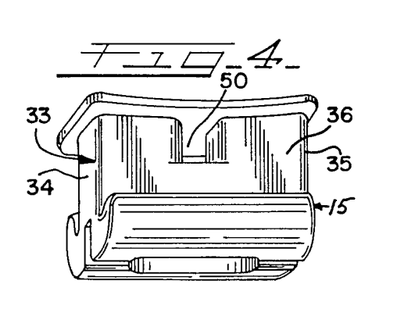
FIG. 4 is a top perspective view of the bracket of FIG. 1 and illustrating the vertical slot.

As illustrated particularly in FIG. 4, a generally vertically extending slot 50 is provided at the rear of the bracket and extends through the base portion 33 for the purpose of accommodating the tail of an uprighting spring or a suitable pin used for attaching an auxiliary to the bracket. Such a slot is optional and a convenience for certain operations during treatment. It may be appreciated that the mouth or inlet end of the slot 50, as seen in FIG. 4, is belled to enhance guiding of a pin or spring tail into the slot. The other end could likewise be belled if desired.

The scoopout 26 is sized to be vertically wider than the archwire slot 24 and of a depth that is at least equal to and usually greater than the depth of the archwire slot. More particularly, the scoopout is illustrated as elongated in shape and generally oval, although it may take other shapes including a spheroidal shape as seen as FIG. 15, and it includes opposed walls 54 and 55 respectively spaced away from the opposed walls 28 and 29 of the archwire slot and toward the respective tie wing tip edges 21a and 22a so that there will not be any contact between the bracket and the upper and lower surfaces of the archwire in the areas of the scoopout 26. Therefore, the friction between the archwire and the archwire slot 24 is limited to that caused by the contact of the archwire with the archwire slot segments 24a and 24b, where in all heretofore known single tie wing brackets a continuous or solid archwire slot is provided between the mesial and distal edges of the bracket. It will be appreciated that the friction between the archwire and the bracket in the present invention is substantially reduced over that of prior known single tie wing brackets.

Further, the scoopout includes a bottom wall 56 that is substantially coplanar with the bottom wall 30 of the archwire slot 24. Depending upon the bracket for a particular tooth, some of the brackets may have the bottom wall of the scoopout situated substantially coplanar with the bottom wall of the archwire slot, while in FIG. 3 it is noted that the bottom wall 56 of the scoopout is actually deeper than that of the archwire slot. Preferably, it is always deeper. In such brackets, the friction between the archwire and the bracket is even further reduced where the archwire would be sliding on the bottom of the slot. It will be appreciated that reducing the friction between the archwire and the bracket facilitates tooth movement and tooth movement objectives, thereby improving the efficiency of the bracket. Additionally, inasmuch as the friction is reduced, thereby reducing anti-archwire sliding forces, desired tooth movements may be accomplished much faster and with greater patient comfort. Whenever patient comfort is improved, patient cooperation is likewise improved, all of which leads to quicker and faster results as well as better overall results in treatment.

While it is preferable to make the bracket of the present invention from metal by suitable casting methods, it will be appreciated that it could be molded or otherwise made of plastic or ceramic. In any event, during the making of the bracket it may be cast in a form that will not include the slot, so that any desired size and/or configuration may be cut into the bracket. In this case, the bracket is first cast and suitably processed so that it can be prepared for cutting a slot. Yet, it should be appreciated that individual brackets may be cast or molded entirely, whereby the slot would be formed by casting or molding. Because of the scoopout 26, where the slot is thereafter cut, it is much easier to cut the slot since there is not as much material to be removed. This contrasts with a heretofore known single wing bracket where a solid slot would be cut from side to side of the bracket. Facilitating the cutting of the slot enables the slot to be cut quicker and reduces the wear on the cutting tool, all of which contributes to the efficiency of making the bracket.

While the bracket illustrated in FIGS. 1 to 4 could be used on a lower anterior tooth, it is illustrated on an upper left canine. Still more particularly, this bracket is particularly useful on narrow teeth, while the wider bracket illustrated in the embodiment of FIGS. 5 to 9 would be used on average sized teeth, and the bracket of extra width illustrated in FIGS. 10 to 14 would be used on the widest teeth.

The height of the scoopout 26, taken generally along the vertical, will always be slightly greater than the corresponding vertical dimension of the archwire slot so that the corresponding sides of the archwire received by the slot will not contact the walls of the scoopout. This thereby limits the friction developed to the friction generated between the archwire and the archwire slot segments, as the wire slides mesiodistally. Further, the depth of the scoopout for a bracket designed for a central may be substantially coplanar with the bottom of the archwire slot since this bracket would preferably be overall less deep than other brackets, but the scoopout would be deeper than the slot in other brackets, thereby still further reducing the friction between the archwire and the bracket.

Figure 15:
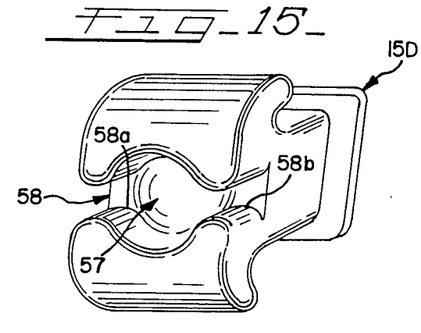
FIG. 15 is a perspective view of another embodiment having a spheroidal scoopout and curvilinear archwire slot walls.

The modified bracket 15D in FIG. 15 differs from bracket 15 in that the scoopout is spheroidal instead of oblong or oval, and the walls of the archwire slot segments are curvilinear instead of flat. Bracket 15D includes a spheroidal scoopout or pocket 57, and an archwire slot 58 defined by archwire slot segments 58a and 58b. The slot segments are aligned and coact to define a segmented archwire slot. Each set segment includes opposed curvilinear or convex walls that define line contact with the archwire and even further reduce sliding friction between the bracket and archwire. Otherwise, this bracket will function like bracket 15.

Reference will now be made to the embodiment illustrated in Figs. 5 to 9 where the bracket is generally designated by the numeral 15A, and which while including all of the features in the bracket of FIGS. 1 to 4, additionally includes notches in the tie wing tips for accommodating ligatures at each side of the bracket and diagonally. This bracket would be slightly wider than that of the embodiment of FIGS. 1 to 4 and therefore usable on a wider tooth. It is also illustrated on an upper left canine. This bracket includes a single tie wing 60 that is generally like the single tie wing in the bracket 15 except for being of slightly greater width and except that it includes notches in the upper and lower tie wing tips 61 and 62. It is likewise illustrated as being mounted on a base or pad 16 which accordingly would be sized to appropriately fit the bracket. The bracket includes an archwire slot 63 having alinged archwire slot segments 63a and 63b and a scoopout 64, both of which would be similar to the slot and scoopout configurations in the embodiment of FIG. 1.

Figure 5:
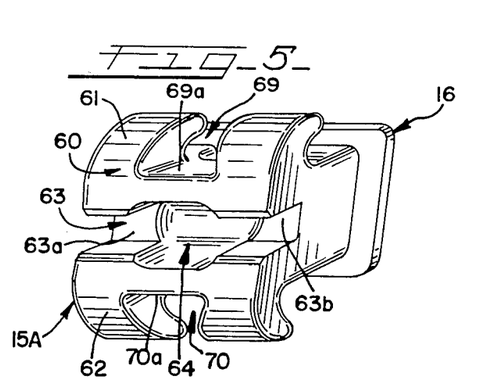
FIG. 5 is a perspective view of a further embodiment of the invention which differs from the embodiment of FIG. 1 in that notches are provided in the tie wing tips.

The primary difference between this embodiment and the bracket 15 is that an upper notch 69 is provided in the upper tie wing tip 61 and a lower notch 70 is provided in the lower tie wing tip 62 so that with respect to receiving ligatures and with respect to the manner in which the archwire is attached to the bracket by one or more ligatures, the bracket will function like a twin tie wing or multiple tie wing bracket. While the notches 69 and 70 are preferably aligned as illustrated, they may be offset if desired.

The converging side walls of the notches result in less "break" or discontinually in the gingival or incisal edges of the bracket. This promotes patient comfort, as the edges of the bracket are then smoother and more continuous. Each notch is wide enough at its mouth so that a ligature can be inserted, and wider at its base so as to accommodate at least two ligatures.

Figure 6:
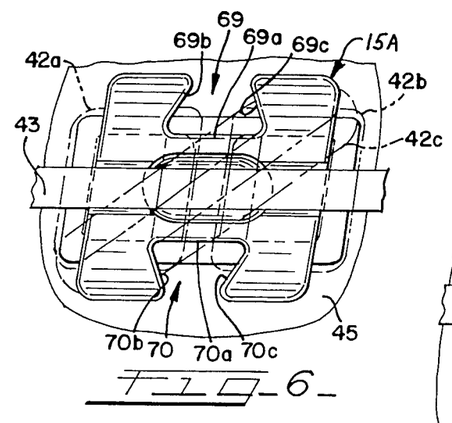
FIG. 6 is a front elevational view of the bracket of FIG. 5 mounted on a tooth and illustrating an archwire received in the archwire slot and a plurality of elastomeric ligatures in phantom to illustrate some of the choices that may be made with respect to the mounting of a ligature on the bracket.
Figure 7:
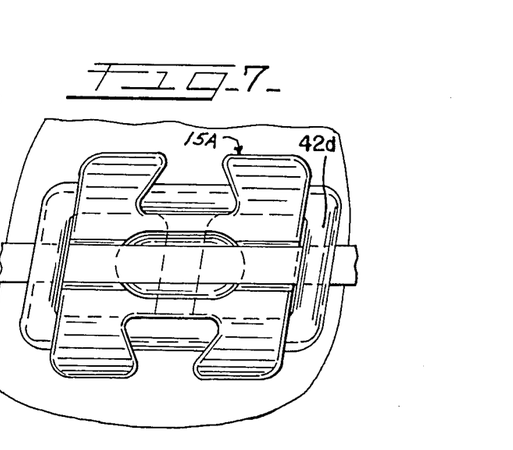
FIG. 7 is a view similar to FIG. 6 but showing a still further selected use of an elastomeric ligature tie.
Figure 8:
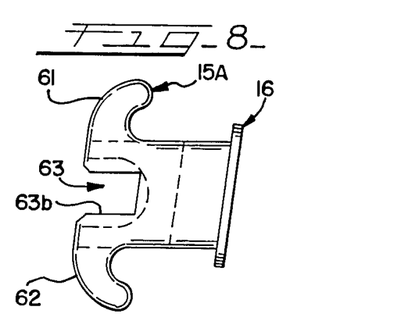
FIG. 8 is a side elevational view of the bracket of FIG. 5.
Figure 9:
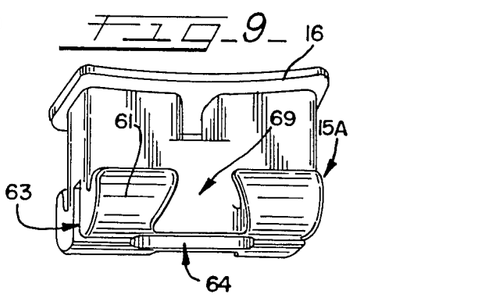
FIG. 9 is a top perspective view of the bracket of FIG. 5 and illustrating the vertical slot at the rear of the bracket.
Figure 10:
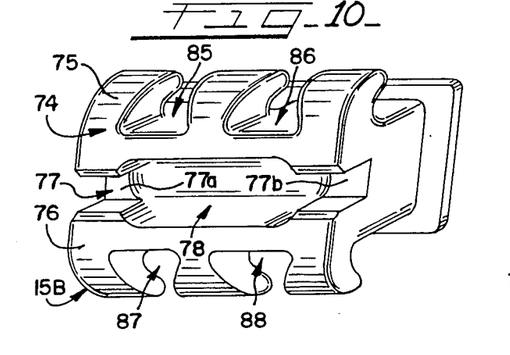
FIG. 10 is a perspective view of a still further modification of the invention wherein plural notches are formed in each of the tie wing tips.

As seen particularly in FIG. 6, the notches 69 and 70 are dove-tail shaped when viewed from the labial or front of the bracket and defined by generally horizontally extending bottom walls 69a and 70a and opposed inwardly inclined side walls 69b, 69c and 70b, 70c. The mesiodistal width of the notches at the upper and lower edges of the tie wing tips is sufficient to enable a standard ligature to fit into the notches. While the width of the notches at the bottom walls is greater in order to facilitate the attachment of plural ligatures, it will be appreciated that the notches do not extend all the way to the scoopout, thereby maintaining the integrity of the single tie wing structure and adding to the overall strength of the bracket.

When a ligature is mounted at one side of the bracket, such as illustrated by ligatures 42a and 42b in FIG. 6, or diagonally of the bracket, as illustrated by ligature 42c, where one run or leg of the ligature extends across the face of the bracket, the pressure of the ligature across the outer face of the archwire is reduced, thereby further reducing the friction between the archwire and the ligature. The ligature 42a has one run at the side of the bracket going directly over the archwire and somewhat against the outer face and sides of the archwire, and one run extending between the notches that is maintained so that it will at the most only engage the outer face of the archwire. Ligature 42b sits in the same fashion, while ligature 42c extending diagonally of the bracket disposes both runs of the ligature across the face of the bracket so that they will only engage the outer face of the archwire. It will be appreciated that a ligature may be disposed diagonally in the opposite direction to that of ligature 42c. Heretofore known twin tie wing brackets would have a greater frictional problem between the archwire and the ligatures whether disposed on one or the other of the tie wings or diagonally across the tie wings, as in these situations both runs of the ligature would be engaging the front face of the archwire as well as parts of the side faces. Finally, it will be appreciated that a ligature as illustrated by ligature 42d in FIG. 7 may be conventionally disposed on the bracket where it includes runs at opposite sides of the bracket and behind the entire portions of both tie wing tips.

A further embodiment of the invention is illustrated in FIGS. 10 to 14, wherein the bracket, generally designated by the numeral 15B, differs from the bracket 15A in that it is slightly wider and includes a plurality of notches in each of the tie wing tips. This embodiment illustrates that any number of notches may be formed in each of the tips, and it should further be appreciated that, if desired, a single notch could be formed in one of the tips, while plural notches could be formed in the other tip.

Bracket 15B likewise includes a single tie wing 74 like the other embodiments and having upper and lower tie wing tips 75 and 76. The tie wing also includes a labially archwire slot 77 defined by aligned archwire slot segments 77a and 77b and centrally disposed to define the wing tips of substantially equal size and a central scoopout or pocket 78. As in the other embodiments, and as illustrated particularly in FIG. 13, the height of the scoopout is greater than the vertical dimension of the slot and the depth is slightly greater than the depth of the slot, thereby defining two slot segments which are in alignment and which coact to define the archwire slot for the bracket.

Figures 11, 12, 14:
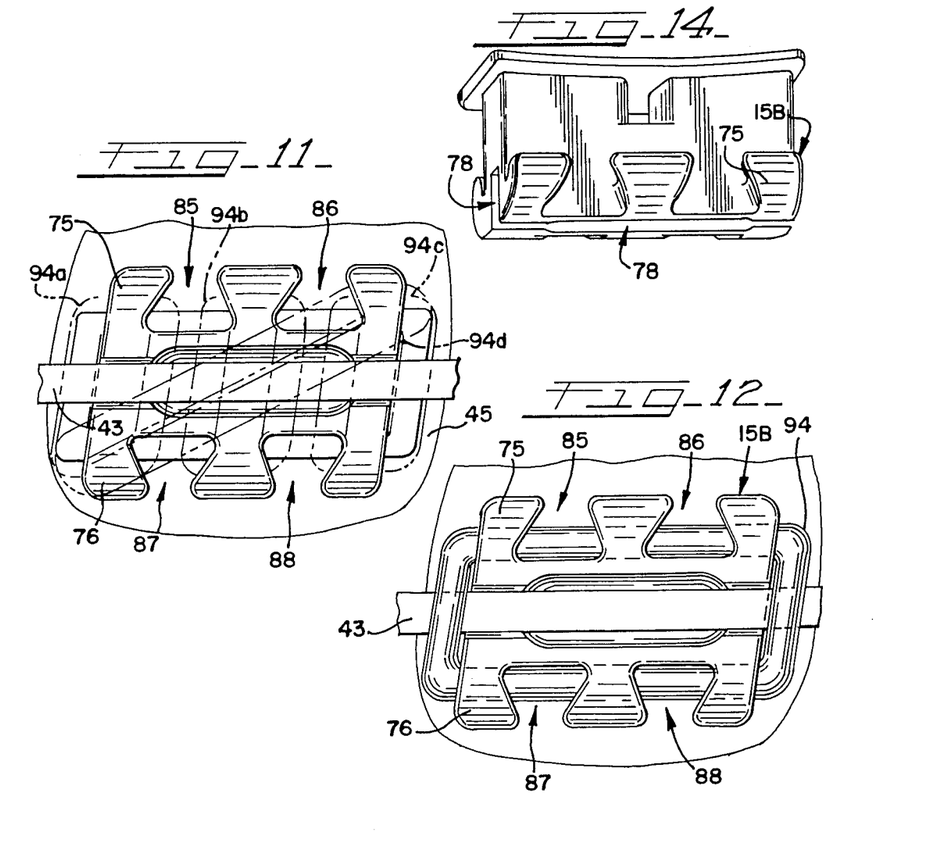
FIG. 11 is a front elevational view of the bracket of FIG. 10 mounted on a tooth and illustrating several choices of ligature positions in phantom.
FIG. 12 is a view similar to FIG. 11 but illustrating a choice of ligature mounting where the ligature goes behind each of the tie wing tips.
FIG. 14 is a top perspective view of the bracket of FIG. 10 and illustrating the vertical slot at the rear of the bracket.
Figure 13:
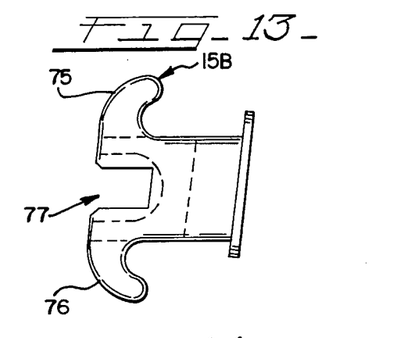
FIG. 13 is a side elevational view of the bracket shown in FIG. 10.

Notches 85 and 86 are provided in the upper tie wing tip 75, while notches 87 and 88 are provided in the lower tie wing tip. It will be appreciated that notches 85 and 87 are in opposed and substantially aligned position, as are notches 86 and 88; and further that notches 85 and 88 are offset from each other, as are notches 86 and 87. This multiple notch arrangement permits a large variety of choices for mounting one or more ligatures. In order to provide an equal force along the archwire to maintain it in the archwire slot, a single ligature 94 is employed, as shown in FIG. 12, whereby the opposite side runs extend along the mesial and distal sides of the bracket and the upper and lower runs extend entirely behind the upper and lower tie wing tips. For other desired objectives, the archwire may be tied to the bracket by use of one or more ligatures, as shown in FIG. 11.

The variety of ligature placements in bracket 15B is even greater than that of bracket 15A because of the increased number of ligature notches in the tie wing tips. Where it is desired to apply a force to urge the archwire into the entire archwire slot 77, the ligature is applied over and behind each of the tie wing tips, as illustrated by the ligature 94 in FIG. 12. In this arrangement, the ligature does not then enter any of the tie wing notches at the tips. Where it is desired to otherwise retain a part or all of the archwire 43 in the archwire slot 77, one or more ligatures may be used such as ligatures 94a, 94b, 94c or 94d, depending upon the type of interconnection desired between the archwire and the bracket. Where one of the runs or legs of ligatures 94a and 94c extend across the face of the bracket, a reduction in friction between the ligature and the archwire is produced, as only one of the runs extends across and over part of the sides of the archwire. Where it would be desirable to reduce friction but still urge the archwire into the entire slot, a combination of ligatures 94a and 94c could be used. It may be appreciated that only ligature 94b may be desired in some instances where the minimum amount of friction is produced between the archwire and the ligature and to primarily hold the center of the archwire relative to the bracket at the center of the bracket. Use of only one ligature at any side of the bracket or at the center would define the lowest force component between the wire and the bracket. It may also be noted that use of ligature 94d diagonally across the face of the bracket through tip notches 86 and 87 would be an alternative method of applying force to the archwire at the center of the bracket and reducing friction because the two runs of the ligature would be supported by the labial face of the bracket and only at the most engage the outer face of the archwire. It will be appreciated that a ligature may be diagonally disposed opposite to that of ligature 94d where it would be inserted through tip notches 85 and 88, or it may even be diagonally disposed where it would be inserted on one side of tip notches 85 and 86 and on the other side tip notch 88, or in the other direction on tip notch 87.

The embodiments illustrated also include a rhomboidal buccolabial or front face and a rhomboidal buccolingual side face, as looking respectively at a front elevational view of the bracket and a side elevational or end elevational view of the bracket. Not all brackets of the present invention for a particular patient would include both or either of the rhomboidal shapes, although it would be appreciated that the frontal rhomboidal shape builds in an angulation of the archwire slot to the bracket. Thus, changing of the frontal rhomboidal shape may increase or decrease the angulation, and when the front face is rectangular, there would be no angulation to the archwire slot. Similarly, the rhomboidal buccolingual profile builds in a torque into the bracket for the archwire slot, and in some forms there would be no torque, while in other forms there would be greater torque than illustrated.

It should also be noted that each of the embodiments has rounded edges and smooth surfaces to enhance patient comfort. Particularly, it may be noted relative to the embodiment of FIG. 1, and this would apply to the other embodiments that the front surface of the tie wing merges with the side surfaces in a rounded edge, and the upper and lower surfaces of the base portion 35 merge with the side walls in rounded edges. Additionally, the entry edges of the archwire slot are beveled or rounded to reduce sharp surfaces. Likewise, the entry edges of the scoopout may be beveled or rounded. All of the rounded or beveled edges would enhance patient comfort.

While the bracket is illustrated with a rectangular archwire, it should be appreciated that it could be used with a round archwire if desired.

From the foregoing, it will be appreciated that the bracket of the invention is an improvement over prior known brackets because it is configured to reduce sliding friction between the archwire and the bracket, and is of a single wing configuration to maximize strength while having the advantage of plural wing brackets. It is also formed to provide greater patient comfort.

It will be understood that modifications and variations may be effected without departing from the scope of the novel concepts of the present invention, but it is understood that this application is to be limited only by the scope of the appended claims.

The invention is hereby claimed as follows:

1. An orthodontic bracket of the edgewise type comprising, a body having a single tie wing, said tie wing having occlusal and gingival tie wing tips, a mesiodistally extending and labially opening archwire slot having occlusal and gingival walls, a scoopout opening to the labial and along said slot and intermediate the ends thereof, and said scoopout being sized to reduce the archwire contacting surfaces of the slot, whereby the sliding friction generated between the archwire and the bracket during movement of the bracket along the archwire is reduced thereby enhancing tooth movements and patient comfort.

2. The bracket of claim 1, wherein the archwire slot is parallel to the edge of the occlusal tie wing tip.

3. The bracket of claim 1, wherein the archwire slot is parallel to the edge of the gingival tie wing tip.

4. The bracket of claim 1, wherein the archwire slot is disposed centrally such that the tie wing tips are of substantially equal size.

5. The bracket of claim 1, wherein the occlusal and gingival edges of said tips are substantially parallel.

6. The bracket of claim 1, wherein said scoopout is substantially oval in shape with the long axis paralleling said slot.

7. The bracket of claim 1, wherein said scoopout includes opposed gingival and occlusal walls generally paralleling said slot and disposed respectively occlusally and gingivally of the occlusal and gingival archwire slot walls.

8. The bracket of claim 7, wherein said scoopout further includes a bottom wall disposed substantially coplanar with the bottom wall of the slot.

9. The bracket of claim 7, wherein said scoopout further includes a bottom wall spaced lingually of the bottom wall of said slot.

10. The bracket of claim 9, wherein said scoopout is substantially oval in shape with the long axis paralleling said slot.

11. The bracket of claim 1, wherein at least one of said tie wing tips includes a notch sized to receive a ligature.

12. The bracket of claim 1, wherein both said tie wing tips include a notch sized to receive a ligature.

13. The bracket of claim 1, wherein both said tie wing tips include a plurality of notches sized to receive a ligature.

14. The bracket of claim 1, wherein the scoopout is substantially spheroidal in shape.

15. The bracket of claim 1, wherein said slot walls are flat.

16. The bracket of claim 1, wherein said slot walls are curvilinear.

17. The bracket of claim 1, wherein said slot walls are convex and define line contact with the archwire.

18. The bracket of claim 11, wherein said notch is dove-tail shaped.

19. The bracket of claim 12, wherein said notches are dove-tail shaped.

20. The bracket of claim 13, wherein said notches are dove-tail shaped.

21. An orthodontic bracket comprising, a body including a single tie wing shaped rhomboidally when viewed from the labial, said tie wing having occlusal and gingival tie wing tips, an archwire slot in said tie wing facing labially and being parallel to occlusal and gingival edges of said tie wing tips and disposed centrally such that said tips are of equal size, a centrally disposed pocket or scooped out portion in the labial of the tie wing and the archwire slot defining a pair of spaced and aligned slot segments, and at least one ligature retention notch in each of the occlusal and gingival edges of said tie wing tips whereby the sliding friction generated between the archwire and the bracket during movement of the bracket along the archwire is reduced thereby enhancing tooth movements and patient comfort.

22. The bracket of claim 21, wherein the notches are aligned.

23. The bracket of claim 21, wherein the notches are offset.

24. An orthodontic bracket of the edgewise type comprising, a body having a single tie wing, said tie wing having occlusal and gingival tie wing tips, a mesiodistally extending and labially opening archwire slot, said slot being disposed centrally of said tie wing, and a scoopout disposed centrally of said tie wing and intermediate the mesial and distal ends of said archwire slot defining the slot as including spaced slot segments and said scoopout being sized to reduce the archwire contacting surfaces of the slot, whereby the sliding friction generated between the archwire and the bracket during movement of the bracket along the archwire is reduced thereby enhancing tooth movements and patient comfort.

* * * * *

UNITED STATES PATENT AND TRADEMARK OFFICE
CERTIFICATE OF CORRECTION

PATENT NO. : 4,799,882

DATED : January 24, 1989

INVENTOR(S) : Peter C. Kesling

It is certified that error appears in the above-identified patent and that said Letters Patent is hereby corrected as shown below:

```
Col. 2, line 55, change "free" to --face--;
        line 61, change "the" to --like--;

Col. 7, line 19, change "discontinually" to --discontinuity--;

Col. 8, line 13, after "labially" insert --opening--;
        line 15, change "the" to --tie--;
```

Signed and Sealed this

Thirtieth Day of May, 1989

Attest:

DONALD J. QUIGG

Attesting Officer

Commissioner of Patents and Trademarks